United States Patent
Farazi et al.

(10) Patent No.: US 7,738,956 B1
(45) Date of Patent: Jun. 15, 2010

(54) PACING SCHEMES FOR REVEALING T-WAVE ALTERNANS (TWA) AT LOW TO MODERATE HEART RATES

(75) Inventors: Taraneh Ghaffari Farazi, San Jose, CA (US); Gene A. Bornzin, Simi Valley, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 568 days.

(21) Appl. No.: 11/341,086

(22) Filed: Jan. 27, 2006

(51) Int. Cl.
*A61N 1/362* (2006.01)
(52) U.S. Cl. .......................................... 607/9
(58) Field of Classification Search .................. 607/9, 607/15, 25, 28
See application file for complete search history.

(56) References Cited

U.S. PATENT DOCUMENTS

| | | |
|---|---|---|
| 4,556,062 A | 12/1985 | Grassi et al. |
| 4,665,919 A | 5/1987 | Mensink et al. |
| 4,766,902 A | 8/1988 | Schroeppel |
| 4,802,491 A | 2/1989 | Cohen et al. |
| 4,974,598 A | 12/1990 | John |
| 5,097,832 A | 3/1992 | Buchanan |
| 5,148,812 A | 9/1992 | Verrier et al. |
| 5,197,480 A | 3/1993 | Gebhardt |
| 5,265,617 A | 11/1993 | Verrier et al. |
| 5,300,092 A | 4/1994 | Schaldach |
| 5,330,507 A | 7/1994 | Schwartz |
| 5,391,187 A | 2/1995 | Freeman |
| 5,437,285 A | 8/1995 | Verrier et al. |
| 5,466,254 A | 11/1995 | Helland |
| 5,476,483 A | 12/1995 | Bornzin et al. |
| 5,547,285 A | 8/1996 | Hutzel et al. |
| 5,549,650 A | 8/1996 | Bornzin et al. |
| 5,560,370 A | 10/1996 | Verrier et al. |
| 5,570,696 A | 11/1996 | Arnold et al. |
| 5,658,317 A | 8/1997 | Haefner et al. |
| 5,772,691 A | 6/1998 | Routh et al. |
| 5,842,997 A | 12/1998 | Verrier et al. |
| 5,861,012 A | 1/1999 | Stroebel |
| 5,921,940 A | 7/1999 | Verrier et al. ............... 600/518 |
| 5,983,138 A | 11/1999 | Kramer |
| 6,016,443 A | 1/2000 | Ekwall |
| 6,058,328 A | 5/2000 | Levine et al. |
| 6,169,919 B1 | 1/2001 | Nearing et al. |
| 6,253,107 B1 | 6/2001 | Albrecht et al. |

(Continued)

FOREIGN PATENT DOCUMENTS

WO    WO 0234123 A2    2/2002

(Continued)

OTHER PUBLICATIONS

Bronzino, the Biomedical Engineering Handbook, CRC Press, 2$^{nd}$ Edition, vol. 1, p. 77-1.

(Continued)

*Primary Examiner*—Carl H Layno
*Assistant Examiner*—Gary A Porter, Jr.
(74) *Attorney, Agent, or Firm*—Theresa Takeuchi

(57) ABSTRACT

Implantable systems that can monitor myocardial electrical stability, and methods for use therewith, are provided. Also provided are novel pacing sequences that are used in such monitoring. Such pacing sequences are designed to reveal alternans at low to moderate heart rates.

17 Claims, 6 Drawing Sheets

U.S. PATENT DOCUMENTS

| | | | |
|---|---|---|---|
| 6,493,586 B1 | 12/2002 | Stahmann et al. | |
| 6,735,466 B1 | 5/2004 | Haghighi-Mood | |
| 6,823,213 B1 | 11/2004 | Norris et al. | 607/9 |
| 6,865,414 B1 | 3/2005 | Levine | |
| 6,915,156 B2 | 7/2005 | Christini et al. | |
| 6,915,157 B2 | 7/2005 | Bennett et al. | |
| 2001/0007948 A1 | 7/2001 | Stoop et al. | |
| 2001/0020136 A1 | 9/2001 | Sweeney et al. | |
| 2002/0138106 A1 | 9/2002 | Christini et al. | |
| 2002/0143265 A1 | 10/2002 | Ackerman et al. | |
| 2002/0165586 A1 | 11/2002 | Hill | |
| 2003/0060724 A1 | 3/2003 | Thiagarajan et al. | |
| 2003/0060854 A1 | 3/2003 | Zhu | |
| 2003/0199937 A1 | 10/2003 | Carlson et al. | |
| 2004/0158292 A1 | 8/2004 | Sheldon | |
| 2005/0004608 A1* | 1/2005 | Bullinga | 607/9 |
| 2006/0116596 A1 | 6/2006 | Zhou et al. | |

FOREIGN PATENT DOCUMENTS

| | | |
|---|---|---|
| WO | WO 0234123 A3 | 2/2002 |
| WO | WO 2004062486 A2 | 7/2004 |
| WO | WO 2004062486 A3 | 7/2004 |

OTHER PUBLICATIONS

Christini et al., "Endocardial Detection of Repolarization Alternans," IEE Transactions on Biomedical Engineering; vol. 50, No. 7 (2003), pp. 855-862.

Bullinga et al., "Resonant Pacing Improves T-wave Alternans Testing in Patients with Dilated Cardiomyopathy" (Heart Rhythm v1:S129, 2004).

Narayan et al. "Demonstration of the Proarrhythmic Preconditioning of Single Premature Extrastimuli by Use of the Magnitude, Phase and Distribution of Repolarization Alternans" (Circulation. 1999; 100: 1887-1893).

Armoundas et al., Pathophysiological Basis and Clinical Application of T-Wave Alternans, Journal of the American College of Cardiology 2002;40;207-217.

Non-Final Office Action mailed Oct. 31, 2007: Related U.S. Appl. No. 11/229,407.

Final Office Action mailed Apr. 24, 2008: Related U.S. Appl. No. 11/229,407.

Final Office Action mailed Nov. 28, 2008: Related U.S. Appl. No. 11/229,407.

Non-Final Office Action mailed Jan. 15, 2008: Related U.S. Appl. No. 11/229,411.

Final Office Action mailed Sep. 12, 2008: Related U.S. Appl. No. 11/229,411.

Non-Final Office Action mailed Jan. 22, 2008: Related U.S. Appl. No. 11/229,410.

Final Office Action mailed Nov. 24, 2008: Related U.S. Appl. No. 11/229,410.

Non-Final Office Action mailed Jul. 27, 2005: Related U.S. Appl. No. 10/186,069.

Notice of Allowance mailed Nov. 21, 2005: Related U.S. Appl. No. 10/186,069.

Non-Final Office Action mailed Dec. 13, 2005: Related U.S. Appl. No. 10/868,240.

Final Office Action mailed Apr. 28, 2006: Related U.S. Appl. No. 10/868,240.

Non-Final Office Action mailed Aug. 2, 2006: Related U.S. Appl. No. 10/868,240.

Notice of Allowance mailed Mar. 28, 2007: Related U.S. Appl. No. 10/868,240.

Non-Final Office Action mailed Feb. 18, 2009: Related U.S. Appl. No. 11/229,411.

Non-Final Office Action mailed Feb. 10, 2009: Related U.S. Appl. No. 11/229,410.

Atlas of Heart Diseases Arrhythmias: Electrophysiologic Principles, vol. IX, Current Medicine 1996, Fig. 6-16.

Final Office Action mailed Dec. 8, 2009: Related U.S. Appl. No. 11/229,411.

Non-Final Office Action mailed Oct. 27, 2009: Related U.S. Appl. No. 11/229,410.

* cited by examiner

PACING SCHEMES FOR REVEALING T-WAVE ALTERNANS (TWA) AT LOW TO MODERATE HEART RATES

CROSS REFERENCE TO RELATED APPLICATIONS

The present invention relates to the following commonly assigned applications and patents, each of which is incorporated herein by reference: U.S. Pat. No. 7,027,867, issued Apr. 11, 2006, entitled "Implantable Cardiac Device Having a System for Detecting T-Wave Alternan Patterns and Method"; U.S. Pat. No. 7,245,968, entitled "Implantable Cardiac Device Providing Rapid Pacing T Wave Alternan Pattern Detection and Method," issued Jul. 17, 2007; U.S. patent application Ser. No. 11/229,411, entitled "Methods and Systems for Detecting the Presence of T-wave Alternans," filed Sep. 16, 2005;

U.S. patent application Ser. No. 11/229,407, entitled "Methods and Systems for Detecting the Presence of T-wave Alternans," filed Sep. 16, 2005; and U.S. patent application Ser. No. 11/229,410, entitled "Methods and Systems for Detecting the Presence of T-wave Alternans," filed Sep. 16, 2005.

FIELD OF THE INVENTION

The present invention generally relates to an implantable cardiac device that monitors myocardial electrical stability. A specific embodiment of the present invention more particularly relates to such a device capable of detecting T-wave alternan patterns.

BACKGROUND

Electrical alternans relate to the differences in electrical potential at corresponding points between alternate heartbeats. T-wave alternans or alternation is a regular or beat-to-beat variation of the ST-segment or T-wave of an electrocardiogram (ECG) which repeats itself every two beats and has been linked to underlying cardiac electrical instability. Typically, by enumerating all consecutive heart beats of a patient, beats with an odd number are referred to as "odd beats" and beats with an even number are referred to as "even beats." A patient's odd and even heartbeats may exhibit different electrical properties of diagnostic significance which can be detected from an ECG.

The presence of these electrical alternans is significant because patients at increased risk for ventricular arrhythmia's commonly exhibit alternans in the ST-segment and the T-wave of their ECG. Clinicians may therefore use these electrical alternans as a noninvasive marker of vulnerability to ventricular tachyarrhythmias. The term T-wave alternans (TWA) is used broadly to denote electrical alternans such as these. It should be understood that the term encompasses both the alternans of the T-wave segment and the ST-segment of an ECG.

T-wave alternans (TWA) has been demonstrated in many studies as a strong predictor of mortality, independent of left ventricular ejection fraction (LVEF). More specifically, it has become well known that T-wave alternans has predictive value for arrhythmic events such as tachyarrhythmias. Additionally, T-wave alternans has been determined to be an indicator of various forms of disordered ventricular repolarization, including disorders found in patients with cardiomyopathy, mild to moderate heart failure, and congestive heart failure.

T-wave alternans (TWA) may be caused by changes in ion exchange during repolarization. If there is an abrupt change in the repolarization period of one beat, the heart attempts to readjust on the following beat. This is manifested as an alternating change in the action potential duration. In the surface ECG this is seen primarily as a change in T-wave. For an implanted medical device such as a cardiac pacemaker, the intracardiac electrogram (IEGM) also shows a change in T-wave. Thus, the term T-wave as used herein may refer to a portion of the ventricular QRS-T-wave complex that includes the T-wave and the QRS-T segment. The alternating feature of TWA can be detected by examination, for example, of the QT interval, T-wave width, T-wave amplitude and morphology, etc. Whatever the designated portion of the intracardiac electrogram, T-wave alternans refers to an alternating pattern of the wave that can be designated "A-B-A-B-A . . . " where A represents every other cycle and B represents every other alternate cycle. As discussed in the literature, when such an alternating pattern appears, the different rates or forms of repolarization of the ventricular cells are statistically associated with a variety of abnormal cardiac conditions. Further, the alternating repolarization pattern can lead to increased electrical instability and consequent cardiac arrhythmias. Thus, the presence of T-wave alternans is recognized as an indicator of risk for ventricular arrhythmia and even sudden cardiac death (SCD).

In the past, detection of T-wave alternan patterns has been performed using surface ECGs. Implementation of such detection has included the measurement, on a beat-to-beat basis, of the micro-volt level changes in the T-wave amplitude from the surface ECG. Then, a long record of time series of T-waves (~5-10 mins) is transformed into the frequency domain by Fourier series transformation (FFT). A prominent peak in the FFT at 0.5 cycles/beat would verify the existence of a T-wave alternan pattern.

Unfortunately, the above detection method requires the use of medical equipment that must be operated by medical personnel in a medical facility such as a physician's office. The detection requires low noise surface ECG with robust and extensive computation equipment. As a result, T-wave alternan pattern detection has been inconvenient and cumbersome. Given the current state of the art, it is difficult to provide continuous and regular T-wave alternan pattern monitoring.

Many patients who would benefit from T-wave alternan pattern monitoring have an implanted cardiac device such as an implantable defibrillator or a combined defibrillator pacemaker. It would thus be highly desirable if such an implanted device could monitor for T-wave alternan patterns. However, the prior art detection method does not lend itself for such application due to, for example, the required long term monitoring, surface ECG, and robust computational requirements for Fourier series transformation.

In order for an implanted cardiac device to provide T-wave alternan pattern monitoring, there is a need for a new and different approach. Embodiments of the present invention addresses that need.

BRIEF SUMMARY OF THE INVENTION

Embodiments of the present invention relate to implantable systems that can monitor myocardial electrical stability, and methods for use therewith. Embodiments of the present invention are also directed to novel pacing sequences that are used in such monitoring.

In accordance with an embodiment, a patient's heart is paced in accordance with a novel patterned pacing sequence of the present invention, and at least one metric of T-waves is measured in two or more beats that follow each change in beat length. Exemplary T-wave metrics include, but are not limited to, T-wave amplitude, T-wave width, T-wave slope, T-wave area, T-wave morphology, QT interval, and evoked QT interval. Magnitudes of alternation are determined based on the measured T-wave metrics, and myocardial electrical stability is monitored based on the determined magnitudes of alternation. This can include determining, based on the determined magnitudes of alternation, whether T-wave alternans are present. This may also include tracking changes in the magnitudes of alternation as these steps are repeated over time, to thereby track changes in myocardial electrical stability.

In one embodiment, the pacing sequence includes a long beat set of at least one long beat, followed by a short beat set of at least one short beat, followed by a regular beat set of at least one regular beat, wherein each said short beat is shorter than each regular beat, and each regular beat is shorter than each long beat. In one embodiment, the long beat set includes a single long beat, the short beat set includes a single short beat, and the regular beat set includes a plurality of regular beats. In another embodiment, the long beat set includes a plurality of long beats, the short beat set includes a plurality of short beats, and the regular beat set includes a plurality of regular beats. In one embodiment, the long beats in the long beat set have the same beat length, the short beats in the short beat set have the same beat length, and the regular beats in the regular beat set have the same beat length. In another embodiment, the short beat set includes short beats that get successively shorter from the beginning to the end of the short beat set. In still another embodiment, the short beat set includes short beats that get successively longer from the beginning to the end of the short beat set. In a further embodiment, the long beat set includes long beats that get successively longer from the beginning to the end of the long beat set. In still a further embodiment, the long beat set includes long beats that get successively shorter from the beginning to the end of the long beat set.

In another embodiment, the pacing sequence includes a short beat set of a plurality of short beats that get successively shorter or longer from the beginning to the end of the short beat set, followed by a regular beat set of a plurality of regular beats, wherein each short beat is shorter than each regular beat. In a specific embodiment, a long beat set of a plurality of long beats follows the regular beat set, wherein each long beat is longer than each regular beat. The long beat set can include long beats of the same length, long beats that get successively longer from the beginning to the end of the long beat set, or long beats that get successively shorter from the beginning to the end of the long beat set.

In a further embodiment, the patterned pacing sequence includes a short beat set of a plurality of short beats that get successively shorter or longer from the beginning to the end of the short beat set, followed by a long beat set of a plurality of long beats, wherein each short beat is shorter than each long beat. In a specific embodiment, the pacing sequence includes a regular beat set of a plurality of regular beats that follow the long beat set.

This description is not intended to be a complete description of, or limit the scope of, the invention. Other features, aspects, and objects of the invention can be obtained from a review of the specification, the figures, and the claims.

DETAILED DESCRIPTION OF THE INVENTION

The following detailed description of the present invention refers to the accompanying drawings that illustrate exemplary embodiments consistent with this invention. Other embodiments are possible, and modifications may be made to the embodiments within the spirit and scope of the present invention. Therefore, the following detailed description is not meant to limit the invention. Rather, the scope of the invention is defined by the appended claims.

It would be apparent to one of skill in the art that the present invention, as described below, may be implemented in many different embodiments of hardware, software, firmware, and/or the entities illustrated in the figures. Any actual software and/or hardware described herein is not limiting of the present invention. Thus, the operation and behavior of the present invention will be described with the understanding that modifications and variations of the embodiments are possible, given the level of detail presented herein.

Exemplary ICD

Figure 1:
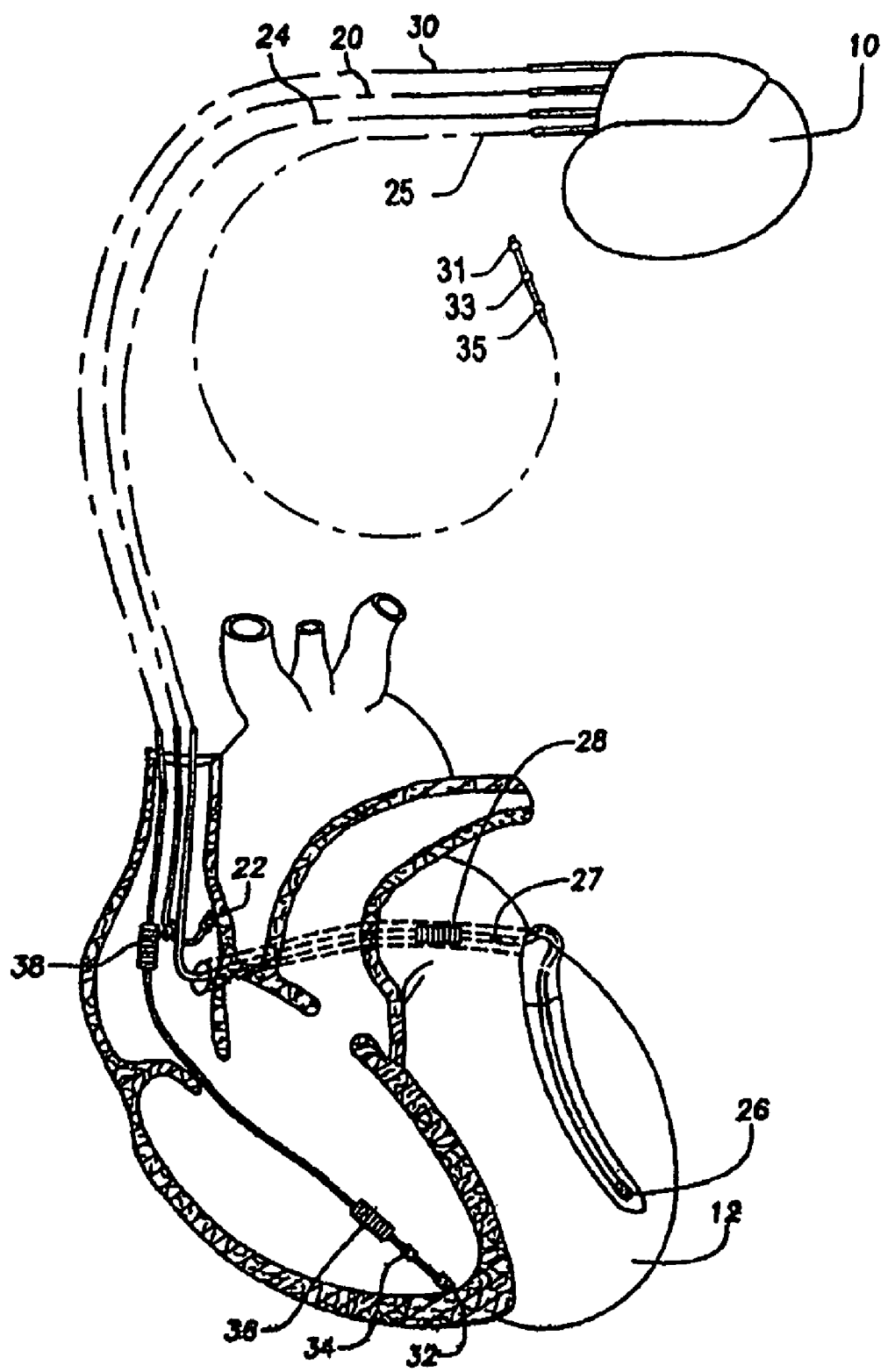
FIG. 1 is a simplified diagram illustrating an exemplary ICD in electrical communication with a patient's heart by means of three leads suitable for delivering multi-chamber stimulation and pacing therapy, and a fourth lead suitable for delivering vagal stimulation.
Figure 2:
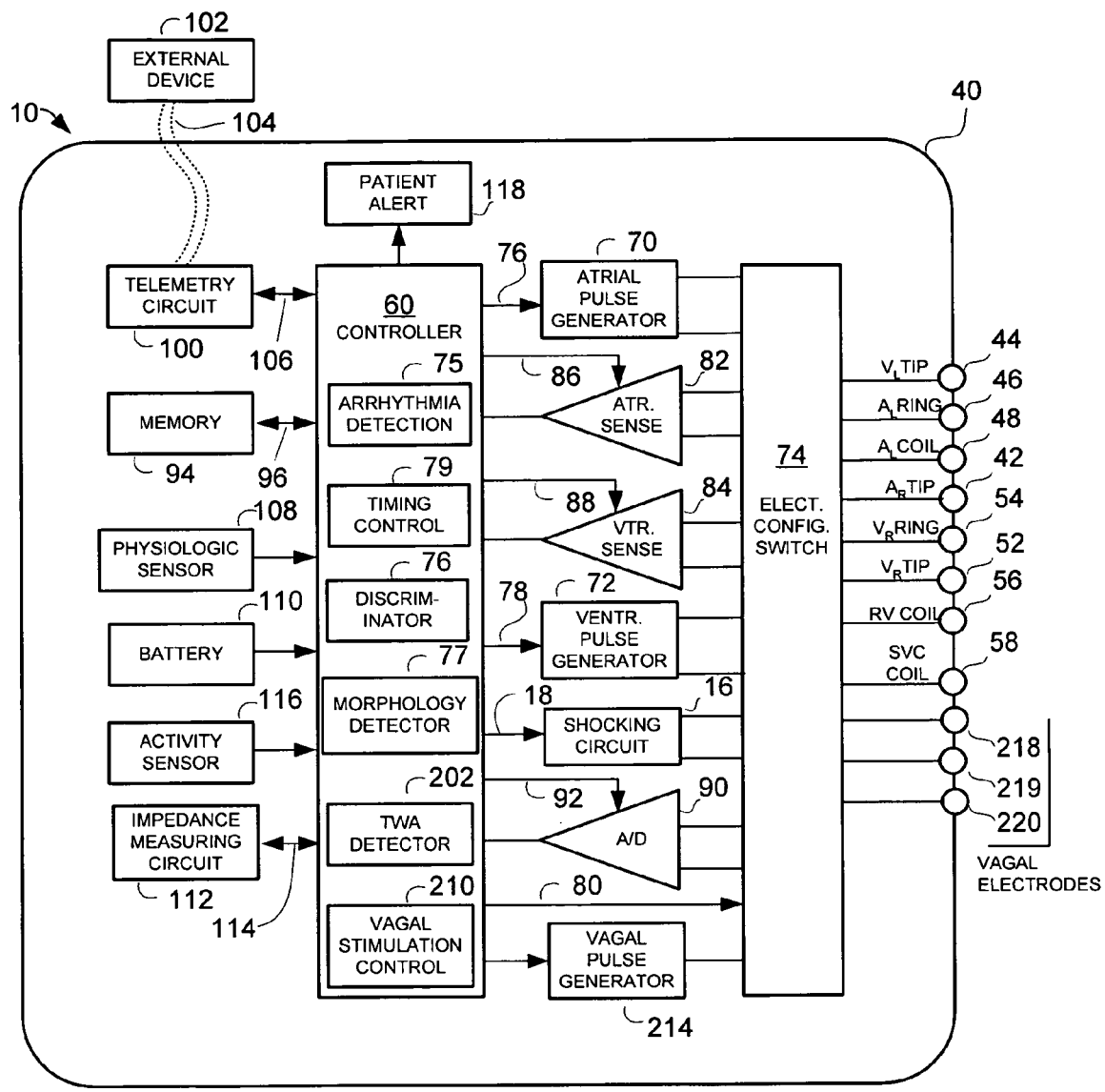
FIG. 2 is a functional block diagram of an exemplary ICD that can provide cardioversion, defibrillation, and pacing stimulation in four chambers of a heart, and monitor myocardial electrical stability, including detect the presence of T-wave alternans, in accordance with embodiments of the present invention.

Before describing the invention in detail, it is helpful to describe an example environment in which the invention may be implemented. The present invention is particularly useful in the environment of an implantable cardiac device that can monitor electrical activity of a heart and deliver appropriate electrical therapy, for example, pacing pulses, cardioverting and defibrillator pulses, and drug therapy, as required. Implantable cardiac devices include, for example, pacemakers, cardioverters, defibrillators, implantable cardioverter defibrillators, and the like. The term "implantable cardiac device" or simply "ICD" is used herein to refer to any implantable cardiac device. FIGS. 1 and 2 illustrate such an environment in which embodiments of the present invention can be used.

Referring first to FIG. 1, an exemplary ICD 10 is shown in electrical communication with a patient's heart 12 by way of three leads, 20, 24 and 30, suitable for delivering multi-chamber stimulation and pacing therapy. To sense atrial cardiac signals and to provide right atrial chamber stimulation therapy, ICD 10 is coupled to implantable right atrial lead 20 having at least an atrial tip electrode 22, which typically is implanted in the patient's right atrial appendage.

To sense left atrial and ventricular cardiac signals and to provide left-chamber pacing therapy, ICD 10 is coupled to "coronary sinus" lead 24 designed for placement in the "coronary sinus region" via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

ICD 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and a superior vena cava (SVC) coil electrode 38. Typically, right ventricular lead 30 is transvenously inserted into heart 12 so as to place the right ventricular tip electrode 32 in the right ventricular apex so that RV coil electrode 36 will be positioned in the right ventricle and SVC coil electrode 38 will be positioned in the SVC. Accordingly, right ventricular lead 30 is capable of receiving cardiac signals and delivering stimulation in the form of pacing and shock therapy to the right ventricle.

In FIG. 1, ICD 10 is also shown as being in electrical communication with the patient's heart 12 by way of a vagal stimulation lead 25, having, e.g., three vagal stimulation electrodes 31, 33, and 35 capable of delivering stimulation bursts to the patient's vagus nerve. Alternatively, vagal stimulation electrodes 31, 33, and 35 can be positioned in the epicardial fat pad near the sinoatrial (SA) node. Based on the description herein, one skilled in the relevant art(s) will understand that the invention can be implemented by positioning vagal stimulation electrodes 31, 33, and 35 in alternate locations, such as in proximity to the cervical vagus, or implanted near or inside the SVC, the inferior vena cava (IVC), or the coronary sinus (CS), where they are also capable of delivering stimulation bursts to the patient's vagus nerve.

FIG. 2 shows a simplified block diagram of ICD 10, which is capable of treating both fast and slow arrhythmias with stimulation therapy, including cardioversion, defibrillation, and pacing stimulation. While a particular multi-chamber device is shown, it is shown for illustration purposes only, and one of skill in the art could readily duplicate, eliminate or disable the appropriate circuitry in any desired combination to provide a device capable of treating the appropriate chamber(s) with the desired cardioversion, defibrillation and pacing stimulation.

A housing 40 of ICD 10, shown schematically in FIG. 2, is often referred to as the "can," "case" or "case electrode" and may be programmably selected to act as the return electrode for all "unipolar" modes. Housing 40 may further be used as a return electrode alone or in combination with one or more of coil electrodes, 28, 36, and 38 for shocking purposes. Housing 40 further includes a connector (not shown) having a plurality of terminals, 42, 44, 46, 48, 52, 54, 56, 58, 218, 219 and 220 (shown schematically and, for convenience, the names of the electrodes to which they are connected are shown next to the terminals). As such, to achieve right atrial sensing and pacing, the connector includes at least a right atrial tip terminal (AR TIP) 42 adapted for connection to atrial tip electrode 22.

To achieve left chamber sensing, pacing and shocking, the connector includes at least a left ventricular tip terminal (VL TIP) 44, a left atrial ring terminal (AL RING) 46, and a left atrial shocking terminal (AL COIL) 48, which are adapted for connection to left ventricular tip electrode 26, left atrial ring electrode 27, and left atrial coil electrode 28, respectively.

To support right chamber sensing, pacing, and shocking the connector also includes a right ventricular tip terminal (VR TIP) 52, a right ventricular ring terminal (VR RING) 54, a right ventricular shocking terminal (RV COIL) 56, and an SVC shocking terminal (SVC COIL) 58, which are configured for connection to right ventricular tip electrode 32, right ventricular ring electrode 34, RV coil electrode 36, and SVC coil electrode 38, respectively.

The connector is also shown as including vagal lead terminals (VAGAL ELECTRODES) 218, 219, and 220, which are configured for connection to vagal stimulation electrodes 31, 33, and 35, respectively, to support the delivery of vagal stimulation bursts.

At the core of ICD 10 is a programmable microcontroller 60, which controls the various modes of stimulation therapy. As is well known in the art, microcontroller 60 typically includes one or more microprocessor, or equivalent control circuitry, designed specifically for controlling the delivery of stimulation therapy and can further include RAM or ROM memory, logic and timing circuitry, state machine circuitry, and I/O circuitry. Typically, microcontroller 60 includes the ability to process or monitor input signals (data) as controlled by a program code stored in a designated block of memory. The details of the design of microcontroller 60 are not critical to the present invention. Rather, any suitable microcontroller 60 can be used to carry out the functions described herein. The use of microprocessor-based control circuits for performing timing and data analysis functions are well known in the art.

Representative types of control circuitry that may be used with the invention include the microprocessor-based control system of U.S. Pat. No. 4,940,052 (Mann et. al.) and the state-machines of U.S. Pat. Nos. 4,712,555 (Sholder) and 4,944,298 (Sholder). For a more detailed description of the various timing intervals used within the ICD's and their inter-relationship, see U.S. Pat. No. 4,788,980 (Mann et. al.). The '052, '555, '298 and '980 patents are incorporated herein by reference.

As shown in FIG. 2, an atrial pulse generator 70 and a ventricular pulse generator 72 generate pacing stimulation pulses for delivery by right atrial lead 20, right ventricular lead 30, and/or coronary sinus lead 24 via an electrode configuration switch 74. It is understood that in order to provide stimulation therapy in each of the four chambers of the heart, atrial and ventricular pulse generators 70 and 72 may include dedicated, independent pulse generators, multiplexed pulse generators, or shared pulse generators. Pulse generators 70 and 72 are controlled by microcontroller 60 via appropriate control signals 71 and 78, respectively, to trigger or inhibit the stimulation pulses.

Also shown in FIG. 2, is a vagal pulse generator 214 that is controlled by vagal stimulation control 210 (within microcontroller 60) via a control signal 212, to trigger or inhibit the delivery of vagal stimulation pulses.

Microcontroller 60 further includes timing control circuitry 79, which is used to control pacing parameters (e.g., the timing of stimulation pulses) as well as to keep track of the timing of refractory periods, PVARP intervals, noise detection windows, evoked response windows, alert intervals, marker channel timing, etc., which are well known in the art. Examples of pacing parameters include, but are not limited to, atrio-ventricular (AV) delay, interventricular (RV-LV) delay, atrial interconduction (A-A) delay, ventricular interconduction (V-V) delay, and pacing rate.

Switch 74 includes a plurality of switches for connecting the desired electrodes to the appropriate I/O circuits, thereby providing complete electrode programmability. Accordingly, switch 74, in response to a control signal 80 from microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to right atrial lead 20, coronary sinus lead 24, and right ventricular lead 30, through switch 74 for detecting the presence of cardiac activity in each of the four chambers of the heart. Accordingly, the atrial (ATR. SENSE) and ventricular (VTR. SENSE) sensing circuits 82 and 84 may include dedicated sense amplifiers, multiplexed amplifiers, or shared amplifiers. Switch 74 determines the "sensing polarity" of the cardiac signal by selectively closing the appropriate switches, as is also known in the art. In this way, a clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables ICD 10 to deal effectively with the difficult problem of sensing the low amplitude signal characteristics of atrial or ventricular fibrillation. Such sensing circuits, 82 and 84, can be used to determine cardiac performance values used in the present invention.

The outputs of atrial and ventricular sensing circuits 82 and 84 are connected to microcontroller 60 which, in turn, are able to trigger or inhibit atrial and ventricular pulse generators, 70 and 72, respectively, in a demand fashion in response to the absence or presence of cardiac activity, in the appropriate chambers of the heart. Sensing circuits 82 and 84, in turn, receive control signals over signal lines 86 and 88 from microcontroller 60 for purposes of measuring cardiac performance at appropriate times, and for controlling the gain, threshold, polarization charge removal circuitry (not shown), and timing of any blocking circuitry (not shown) coupled to the inputs of sensing circuits 82 and 86.

For arrhythmia detection, ICD 10 utilizes the atrial and ventricular sensing circuits 82 and 84 to sense cardiac signals to determine whether a rhythm is physiologic or pathologic. The timing intervals between sensed events (e.g., P-waves, R-waves, and depolarization signals associated with fibrillation are then classified by microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Microcontroller 60 utilizes arrhythmia detector 75 and morphology detector 77 to recognize and classify arrhythmia so that appropriate therapy can be delivered. The morphology detector 77 may also be used to detect signal morphologies that are useful for detecting T-wave alternans, in accordance with embodiments of the present invention described below. The arrhythmia detector 75 and morphology detector 77 can be implemented within the microcontroller 60, as shown in FIG. 2. Thus, these elements can be implemented by software, firmware, or combinations thereof. It is also possible that all, or portions, of these detectors can be implemented using hardware.

Cardiac signals are also applied to the inputs of an analog-to-digital (A/D) data acquisition system 90. Data acquisition system 90 is configured to acquire intracardiac electrogram signals, convert the raw analog data into a digital signal, and store the digital signals for later processing and/or telemetric transmission to an external device 102. Data acquisition system 90 is coupled to right atrial lead 20, coronary sinus lead 24, and right ventricular lead 30 through switch 74 to sample cardiac signals across any pair of desired electrodes.

Data acquisition system 90 can be coupled to microcontroller 60, or other detection circuitry, for detecting an evoked response from heart 12 in response to an applied stimulus, thereby aiding in the detection of "capture." Capture occurs when an electrical stimulus applied to the heart is of sufficient energy to depolarize the cardiac tissue, thereby causing the heart muscle to contract. Microcontroller 60 detects a depolarization signal during a window following a stimulation pulse, the presence of which indicates that capture has occurred. Microcontroller 60 enables capture detection by triggering ventricular pulse generator 72 to generate a stimulation pulse, starting a capture detection window using timing control circuitry 79 within microcontroller 60, and enabling data acquisition system 90 via a control signal 92 to sample the cardiac signal that falls in the capture detection window and, based on the amplitude, determines if capture has occurred. Additionally, microcontroller 60 can detect cardiac events, such as premature contractions of ventricles, and the like.

The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et. al.); and U.S. Pat. No. 5,350,410 (Mann et. al.), which patents are hereby incorporated herein by reference. The type of capture detection system used is not critical to the present invention.

Microcontroller 60 is further coupled to a memory 94 by a suitable data/address bus 96, wherein the programmable operating parameters used by microcontroller 60 are stored and modified, as required, in order to customize the operation of ICD 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to heart 12 within each respective tier of therapy.

The operating parameters of ICD 10 may be non-invasively programmed into memory 94 through telemetry circuit 100 in telemetric communication with external device 102, such as a programmer, transtelephonic transceiver, or a diagnostic system analyzer. Telemetry circuit 100 is activated by microcontroller 60 by a control signal 106. Telemetry circuit 100 advantageously allows intracardiac electrograms and status information relating to the operation of ICD 10 (as contained in microcontroller 60 or memory 94) to be sent to external device 102 through established communication link 104.

For examples of such devices, see U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. Pat. No. 6,275,734, entitled "Efficient Generation of Sensing Signals in an Implantable Medical Device such as a Pacemaker or ICD" (McClure et al.), which patents are hereby incorporated herein by reference.

ICD 10 further includes a physiologic sensor 108 that can be used to detect changes in cardiac performance or changes in the physiological condition of the heart. Accordingly, microcontroller 60 can respond by adjusting the various pacing parameters (such as rate, AV Delay, RV-LV Delay, V-V Delay, etc.). Microcontroller 60 controls adjustments of pacing parameters by, for example, controlling the stimulation pulses generated by the atrial and ventricular pulse generators 70 and 72. While shown as being included within ICD 10, it is to be understood that physiologic sensor 108 may also be external to ICD 10, yet still be implanted within or carried by the patient. More specifically, sensor 108 can be located inside ICD 10, on the surface of ICD 10, in a header of ICD 10, or on a lead (which can be placed inside or outside the bloodstream).

Also shown in FIG. 2 is an activity sensor 116. The activity sensor 116 (e.g., an accelerometer) can be used to determine the activity of the patient. Such information can be used for rate responsive pacing, or, in accordance with embodiments of the present invention, to determine whether the patient is sufficiently at rest such that certain baseline measurements can be obtained. If the sensor 116 is a multi-dimensional accelerometer, then posture information can also be extracted. The following patents, which are incorporated herein by reference, describe exemplary activity sensors that can be used to detect activity of a patient (some also detect posture): U.S. Pat. No. 6,658,292 to Kroll et al., entitled "Detection of Patient's Position and Activity Status using 3D Accelerometer-Based Position Sensor"; U.S. Pat. No. 6,466,821 to Kroll et al., entitled "Orientation of Patient's Position Sensor using External Field"; and U.S. Pat. No. 6,625,493 to Pianca et al., entitled "AC/DC Multi-Axis Accelerometer for Determining Patient Activity and Body Position." Simple activity sensors employ a piezoelectric crystal or a cantilever beam having a film of a piezoelectric polymer adhered to a surface of the beam. These are just a few exemplary types of activity sensors 116, which are not meant to be limiting.

The ICD 10 may also include a magnet detection circuitry (not shown), coupled to microcontroller 60. It is the purpose of the magnet detection circuitry to detect when a magnet is placed over ICD 10. A clinician may use the magnet to perform various test functions of ICD 10 and/or to signal microcontroller 60 that the external programmer 102 is in place to receive or transmit data to microcontroller 60 through telemetry circuit 100.

As further shown in FIG. 2, ICD 10 can have an impedance measuring circuit 112, which is enabled by microcontroller 60 via a control signal 114. The known uses for an impedance measuring circuit 112 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 112 is advantageously coupled to switch 74 so that any desired electrode may be used. The impedance measuring circuit 112 is not critical to the present invention and is shown only for completeness.

In the case where ICD 10 is intended to operate as a cardioverter, pacer or defibrillator, it must detect the occurrence of an arrhythmia and automatically apply an appropriate electrical therapy to the heart aimed at terminating the detected arrhythmia. To this end, microcontroller 60 further controls a shocking circuit 16 by way of a control signal 18. The shocking circuit 16 generates shocking pulses of low (up to about 0.5 Joules), moderate (about 0.5-10 Joules), or high energy (about 11 to 40 Joules), as controlled by microcontroller 60. Such shocking pulses are applied to the patient's heart 12 through at least two shocking electrodes (e.g., selected from left atrial coil electrode 28, RV coil electrode 36, and SVC coil electrode 38). As noted above, housing 40 may act as an active electrode in combination with RV electrode 36, or as part of a split electrical vector using SVC coil electrode 38 or left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of about 5-40 Joules), delivered asynchronously (since R-waves may be too disorganized to be recognize), and pertaining exclusively to the treatment of fibrillation. Accordingly, microcontroller 60 is capable of controlling the synchronous or asynchronous delivery of the shocking pulses.

ICD 10 additionally includes a battery 110, which provides operating power to a load that includes all of the circuits shown in FIG. 2.

TWA Detection

Referring back to FIG. 2, in accordance with embodiments of the present invention, microcontroller 60 includes a T-wave alternan (TWA) detector 202, which as described in more detail below, can detect the presence of T-wave alternans. The TWA detector 202 can be implemented within the microcontroller 60, as shown in FIG. 2. Thus, TWA detector 202 can be implemented by software, firmware, or combinations thereof. It is also possible that all, or portions, of TWA detector 202 can be implemented using hardware. Further, it is possible that all, or portions, of TWA detector 202 be implemented external to the microcontroller 60.

In an embodiment, TWA detector 202 triggers data acquisition circuit 90 and timing control circuit 79 to record IEGM signal information when a patient is paced using patterned pacing sequences of the present invention. TWA detector 202 can measure T-wave metrics, such as T-wave amplitude, T-wave width, T-wave slope, T-wave area, T-wave morphology, QT interval, evoked QT interval, etc. in the IEGM signal generated by the sensing circuits of the data acquisition system 90. TWA detector 202 can also trigger the implantable device 10 to respond appropriately when T-wave alternans are detected, as will be explained in more detail below. Additionally, in conjunction with a telemetry circuit 100, TWA detector 202 can be configured to deliver status information, relating to the patient's T-wave alternans, to an external device 102 through an established communication link 104. TWA detector 202 may also trigger a patient or physician alert in response to detecting T-wave alternans. For example, a patient alert 118, which produces a vibratory or auditory alert, may be triggered by the TWA detector 202.

Figure 3A:
FIG. 3A is an IEGM representation of a pacing scheme that includes a relatively shorter interval periodically once every fourth cycle during a moderately fast and constant pacing routine.
Figure 3B:
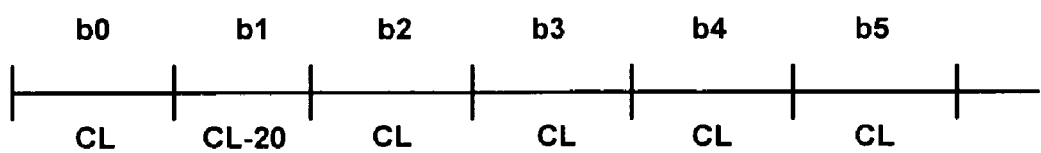
FIG. 3B is a short-hand version of the pacing scheme shown in FIG. 3B.
Figure 3C:
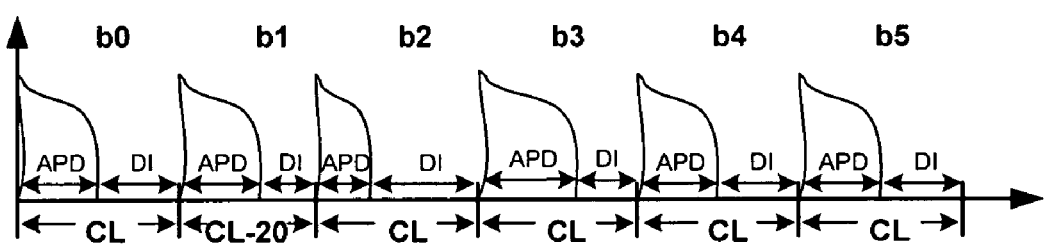
FIG. 3C shows that the pacing scheme of FIGS. 3A and 3B results in a premature ending of a diastolic interval (DI), which in turn causes a shortening followed by a lengthening of an action potential duration (APD) of the subsequent two beats.

T-wave alternans have been demonstrated in many studies to be strong predictor of mortality, independent of left ventricular ejection fraction (LVEF). It has been generally believed that an elevated constant heart rate is a requirement for the detection of T-wave alternans. However, a recent work published by Bulling a et al., entitled "Resonant Pacing Improves T-wave Alternans Testing in Patients with Dilated Cardiomyopathy" (Heart Rhythm v1:S129, 2004) revealed a more robust detection with "resonant pacing" scheme. In this technique, TWA with higher amplitudes were detected by pacing at a relatively shorter interval periodically once every fourth cycle during a moderately fast and constant pacing routine. An ECG representation of such a pacing scheme is shown in FIG. 3A, and a short-hand version of such a pacing scheme is shown in FIG. 3B. Referring to FIG. 3C, this increase in T-wave amplitudes is due to the premature ending of the diastolic interval (DI) which in turn causes a shortening followed by the lengthening of the action potential duration (APD) of the subsequent two beats.

Figure 4:
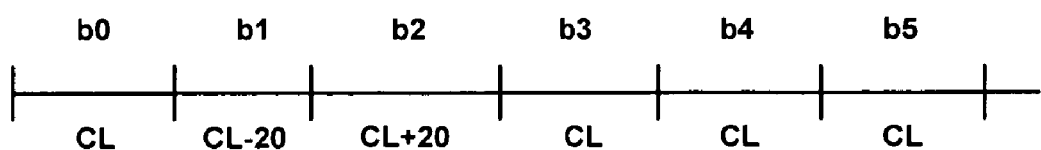
FIG. 4 shows a pacing scheme where every short cycle is immediately followed by a "long" cycle and then back to the base cycle length.

Using this same rational that explains the increased T-wave amplitude following every "short" cycle in this pacing scheme of Bulling a, one can expect to induce an even higher oscillation in T-wave amplitude with a scheme such as that of FIG. 4. The pacing scheme of FIG. 4 is different from the scheme of FIGS. 3A-3C in that every short cycle is immediately followed by a "long" cycle and then back to the base cycle length. A similar scheme is disclosed in U.S. patent application Ser. No. 10/884,276 to Bulling a filed Jul. 2, 2004 (Pub. No.: US 2005/0004608 A1), which is incorporated herein by reference.

Embodiments of the present invention relate to novel "patterned" pacing schemes that can be used for detecting T-wave alternans, and more generally, for monitoring myocardial electrical stability. Embodiments of the present invention also relate to implantable cardiac devices such as pacemakers and/or defibrillators capable of delivering the novel "patterned" pacing schemes and monitoring myocardial electrical stability based on a heart's response to the pacing schemes.

Figure 5:
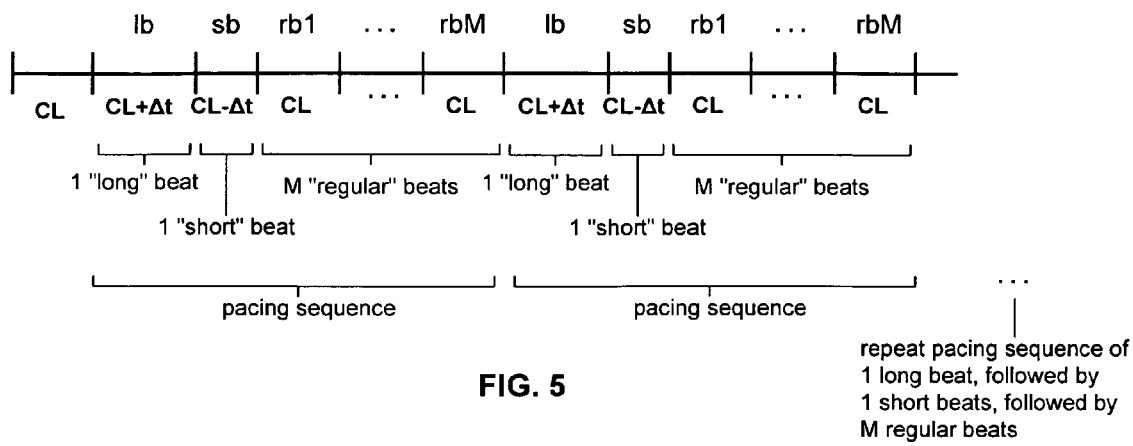
FIG. 5 illustrates a pacing scheme, according to an embodiment of the present invention, where a patterned pacing sequence includes a long beat, followed by a short beat, followed by regular beats.

Referring now to FIG. 5, a patterned pacing sequence according to an embodiment of the present invention includes one "long" cycle, i.e., CL+Δt (also referred to as a long beat), followed by one "short" cycle, i.e., CL−Δt (also referred to as a short beat), followed by a plurality of regular cycles CL (referred to as M regular beats, where M is an integer greater than or equal to 2). In one embodiment, the Δt that is used to produce the long beat length is equal to the Δt that is used to produce the short beat length. In another embodiment, the Δt that is used to produce the long beat is different than the Δt that is used to produce the short beat. After the patterned pacing sequence is repeated a predetermined number of times (or for a predetermined period of time), the patterned pacing is terminated, and constant or no-pacing is resumed.

In FIG. 5, and the following figures, "sb" refers to a short beat, "lb" refers to a long beat, and "rb" refers to a regular beat. The terms "long" and "short" are relative to the "regular" beat. In other words, a long beat is longer than a regular beat, and a short beat is shorter than a regular beat. A regular beat can be thought of as the baseline cycle length CL for a patterned pacing sequence. To ensure capture, the each beat of the patterned pacing sequence should be shorter than an intrinsic beat. Thus, even a long beat should be shorter than an intrinsic beat. By definition then, a regular beat and a short beat are each also shorter than an intrinsic beat. Thus, the length of a long beat is limited by an intrinsic beat length. Additionally, where the patient is normally paced, the short, regular and long beats of the patterned pacing sequence should each be shorter than a beat length corresponding to the patient's normal pacing.

Preferably, a patient is paced using the patterned pacing sequence for at least predetermined amount of time (e.g., one minute) so that sufficient IEGM data can be collected to make meaningful determinations relating to alternations of T-wave metrics. In accordance with embodiments of the present invention, at least one metric of T-waves is measured in two or more beats (e.g., 4 beats) that follow each change in beat length. A likely T-wave metric is T-wave amplitude. However, other T-wave metrics include, but are not limited to, T-wave width, T-wave slope, T-wave area, T-wave morphology, QT interval, and evoked QT interval.

A determination of whether T-wave alternans (TWA) are present can then be based on the T-wave metrics. This can be accomplished, for example, by determining one or more magnitude of alternation, based on the measured T-wave metrics, and then comparing such magnitude(s) of alternation to one or more threshold. Exemplary ways to determine magnitudes of alternation are discussed below. Because T-wave metrics may change in magnitude due to the changes in diastolic intervals (DI) and action potential durations (APD), even in the healthiest of hearts, such threshold(s) should be set at a high enough level to distinguish between alternations in T-wave metrics that are primarily due to the pacing sequence, and those that are due to an instability of the myocardium. Additionally, such threshold(s) is preferably set such that it can distinguish between alternations that are due to actual changes in a metric of T-waves, as opposed to changes due to noise.

As mentioned above, after the patterned pacing sequence is repeated a predetermined number of times (or for a predetermined period of time), the patterned pacing is terminated, and constant or no-pacing is resumed. As also mentioned above, the measured T-wave metrics can be used to determine a magnitude of alternation, which is indicative of myocardial electrical stability. In accordance with an embodiment of the present invention, information indicative of the determined magnitudes of alternation are stored within the implantable device, so that changes in the magnitudes of alternation can be tracked over time. For example, a patient can be continuously paced using the patterned pacing sequence for 5 minutes, once a week, and the determined magnitudes of alternation can be stored, thereby enabling a determination whether the magnitudes of alternation remain relatively constant, increase, or decrease over time. Magnitudes of alternation staying relatively constant would be indicative of myocardial electrical stability remaining relatively constant; increases in the magnitudes of alternation would be indicative of decreases in myocardial electrical stability; and decreases in magnitudes of alternation would be indicative of increases in myocardial electrical stability.

Figure 6:
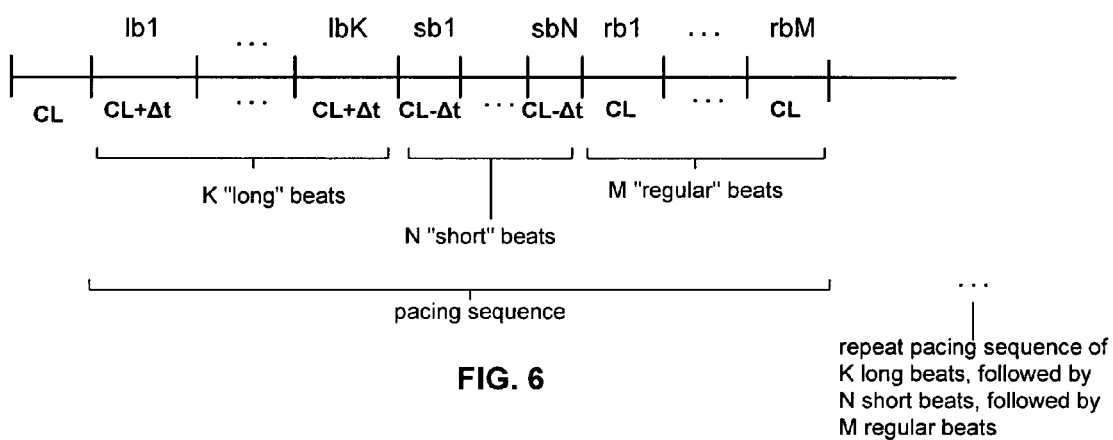
FIG. 6 illustrates a pacing scheme, according to an embodiment of the present invention, where a patterned pacing sequence includes a plurality of long beats, followed by a plurality of short beats, followed by a plurality of regular beats.

Referring now to FIG. 6, a patterned pacing sequence according to another embodiment of the present invention includes a plurality of long beats (i.e., K long beats), followed by a plurality of short beats (i.e., N short beats), followed by a plurality of regular beats (i.e., M regular beats), where K, N and M are integers, each of which are greater than or equal to 2, but need not be equal to one another.

In another embodiment of the present invention, a patterned pacing sequence includes a plurality of short beats, followed by a plurality of long beats, followed by a plurality of regular beats. This sequence would resemble the one shown in FIG. 5, but with the short beats occurring prior to the long beats.

Referring now to FIG. 6, a patterned pacing sequence according to another embodiment of the present invention includes a plurality of long beats (i.e., K long beats), followed by a plurality of short beats (i.e., N short beats), followed by a plurality of regular beats (i.e., M regular beats), where K, N and M are integers, each of which are greater than or equal to 2, but need not be equal to one another. In one implementation, the scheme in FIG. 6 begins by pacing at a basic or regular cycle length of CL. At regular intervals CL is increased by an amount $\Delta t_1$ for K cycles (K>=2, e.g., K=3), and then decreased by an amount $\Delta t_2$ for N cycles (N>=2, e.g., N=3). The amount $\Delta t_1$ may or may not equal the amount $\Delta t_2$. The transition from CL to the $1^{st}$ beat of the K long beats sequence lengthens the DI interval for lb1, causing lengthening of APD and increasing of T-wave amplitude for lb2. The transition from the long beats to the $1^{st}$ beat of the N short beats sequence prematurely ends the DI interval for sb1, causing shortening of APD and lowering of T-wave amplitude for sb2. Similarly, in the transition from the last short beat in the sequence (sbN) back to CL, DI is extended for rb1, leading to the lengthening of the APD and increasing of T-wave amplitude for the next cycle rb2. This decrease and increase in the T-wave amplitude caused by this pacing scheme will be pronounced and easily detectable due to the sudden changes in pacing intervals. Moreover, recent publications have illustrated the role of cardiac memory of at least 2 or more beats. This finding leads the inventors to believe that the effect seen by this pacing scheme should be enhanced especially when K, N and M are greater than 2 beats. Also noted is that this pacing scheme potentially invokes alternans at three points in the sequence: once when it transitions from CL (i.e., regular beats) to long beats, once when it transitions from long beats to short beats, and once when it transitions from short beats back to regular beats (CL).

In still another embodiment of the present invention, a patterned pacing sequence includes one long beat, followed by a plurality of short beats, followed by a plurality of regular beats. This sequence would resemble the one shown in FIG. 6, but with one long beat in place of the plurality of long beats.

In a further embodiment of the present invention, a patterned pacing sequence includes a plurality of long beats, followed by one short beat, followed by a plurality of regular beats. This sequence would resemble the one shown in FIG. 6, but with one short beat in place of the plurality of short beats.

Figure 7:
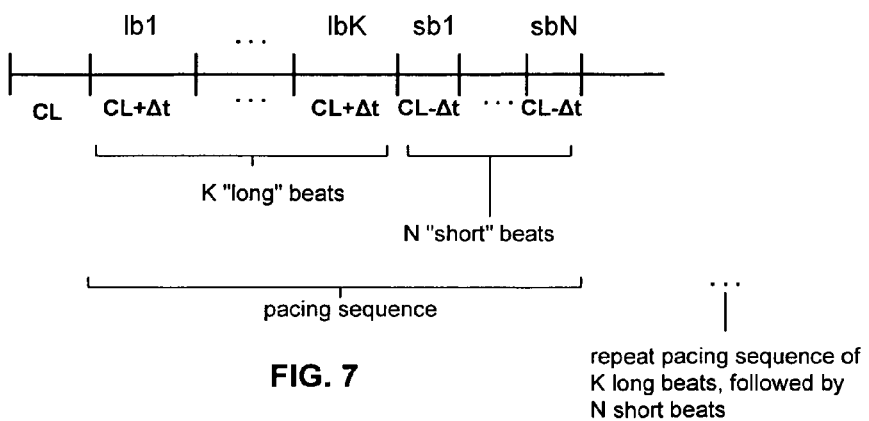
FIG. 7 illustrates a pacing scheme, according to an embodiment of the present invention, where a patterned pacing sequence includes a plurality of long beats, followed by a plurality of short beats.

In another embodiment of the present invention, a pacing sequence includes a plurality of long beats, followed by a plurality of short beats, and the sequence is repeated a plurality of times without regular beats being interspersed. An example of this is shown in FIG. 7.

Figure 8:
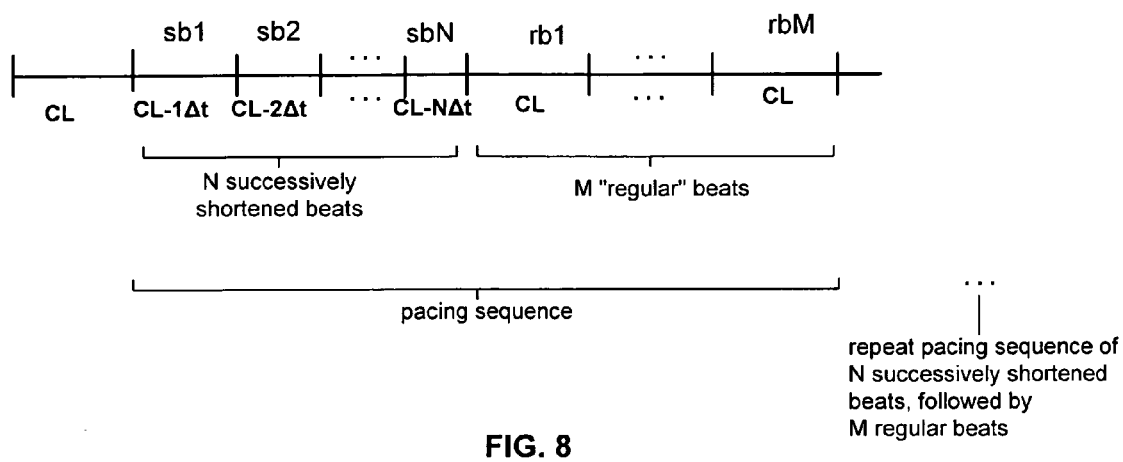
FIG. 8 illustrates a pacing scheme, according to an embodiment of the present invention, where a patterned pacing sequence includes a plurality of successively shortened beats, followed by a plurality of regular beats.

Referring now to FIG. 8, a patterned pacing sequence according to another embodiment of the present invention includes a plurality of successively shortened beats (i.e., N shortened beats, where each successive beat is shorter than the previous beat) followed by a plurality of regular beats. This can be accomplished by defining a $\Delta t$, and making each successive beat another multiple a $\Delta t$ smaller. In other words, the successively shortened beats can be CL-$\Delta t$, CL-2$\Delta t$, CL-3$\Delta t$ etc. Other possibilities for successively shortening beats are also within the scope of the present invention.

Figure 9:
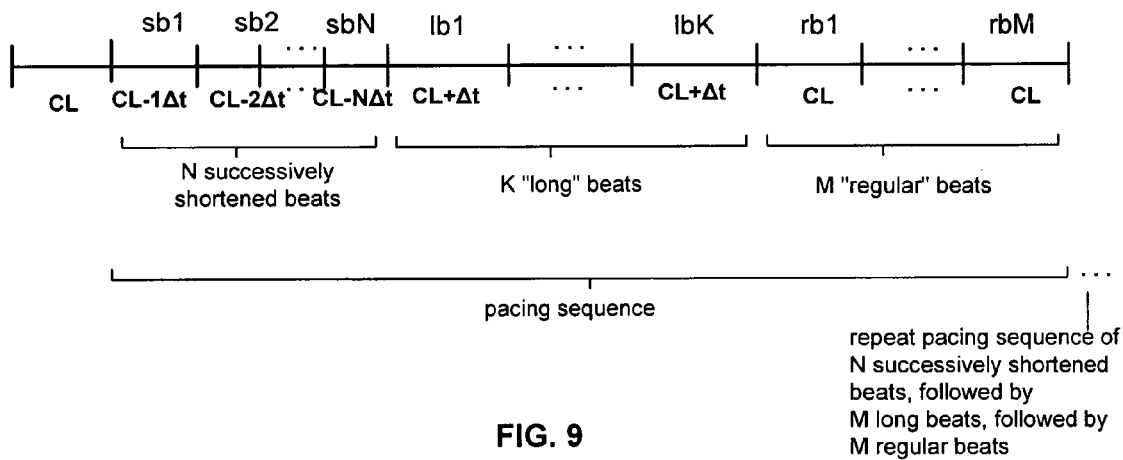
FIG. 9 illustrates a pacing scheme, according to an embodiment of the present invention, where a patterned pacing sequence includes a plurality of successively shortened beats, followed by a plurality of long beats, followed by a plurality of regular beats.

Referring now to FIG. 9, a patterned pacing sequence according to another embodiment of the present invention includes a plurality of successively shortened beats (i.e., N shortened beats, where each successive beat is shorter than the previous beat), followed by a plurality of long beats (i.e., K long beats), followed by a plurality of regular beats.

In other embodiments, the long beats within a long beat set can be successively lengthened (or shortened). It is also possible that short beats within a short beat set can be successively lengthened.

Figure 10:
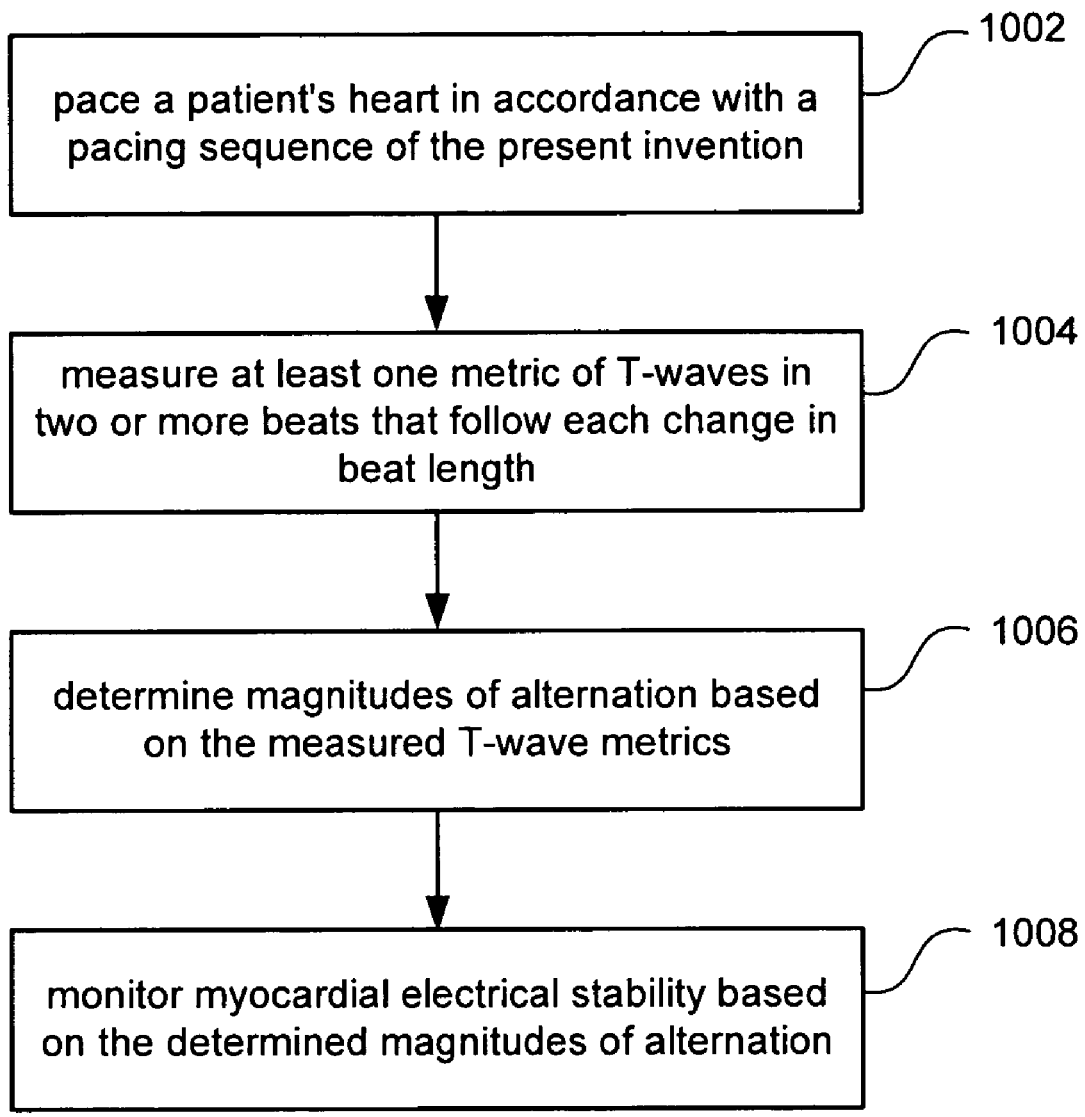
FIG. 10 is a high-level process flowchart that is useful for describing various embodiments of the present invention.

Embodiments of the present invention will now be summarized with reference to the high level flow diagram of FIG. 10. Referring to FIG. 10, at steps 1002 and 1004, a patient's heart is paced in accordance with one of the patterned pacing sequences of the present invention (which have been described above), and at least one metric of T-waves in two or more beats that follow each change in beat length is measured. Preferably, a patterned pacing sequence of the present invention is repeated a predetermined number of times (or for a predetermined period of time) before the patterned pacing is terminated, and constant or no-pacing is resumed. If T-wave alternans are present, they will be detectable, with higher amplitudes, immediately following where there is a change from one beat length to another (e.g., long to short, long to regular, short to long, short to regular, short to shorter, etc.).

At a step 1006, magnitudes of alternation are determined based on the measured T-wave metrics. Still referring to FIG. 10, at a step 1008, myocardial electrical stability is monitored based on the determined magnitudes of alternation. Step 1008 can include determining, based on the determined magnitudes of alternation, whether T-wave alternans are present. Additionally or alternatively, step 1008 can include tracking changes in the magnitudes of alternation as steps 1002, 1004 and 1006 are repeated over time, to thereby track changes in myocardial electrical stability.

Embodiments of the present invention, as can be appreciated from the discussion above, can be thought of as relating to the novel patterned pacing sequences that are designed to increase and decrease the amplitude (and duration) of T-waves at specific points in the sequence. Exemplary techniques are described below that can be used to determine magnitudes of alternation based on the T-wave metrics measured at step 1004. However, it is noted that embodiments of the present invention should not be limited to the specific techniques described.

As explained above, T-wave amplitude and duration is expected to decrease following the first beat where the beat length is shortened relative to a previous beat. Conversely, T-wave amplitude and duration is expected to increase following the first beat where the beat length is lengthened as compared to a previous beat. In one example, using the T-wave metrics measured at step 1004, steps 1006 and 1008 can include lining up all the T-wave metrics of beats where an increase in T-wave amplitude is expected, and lining up all the T-wave metrics of beats where a decrease in T-wave amplitude is expected. Ensemble averaging (or some other averaging) can then be performed to produce one or more average "low" T-wave metric and one or more average "high" T-wave metric. A magnitude of alternation can then be determined by determining a difference between an average "low" T-wave metric and a corresponding average "high" T-wave metric. This difference (i.e., magnitude of alternation) can be compared to a threshold to determine if T-wave alternans are present. If the difference is less than the threshold, then it can be determined that T-wave alternans are not present. If the difference (i.e., the magnitude of alternation) is greater than the threshold, then it can be determined that the T-wave alternans are present. It is also possible to have multiple thresholds such that in addition to determining whether T-wave alternans are present, changes in magnitudes of alternations can be determined. This can be used, e.g., to determine a degree of the T-wave alternans. This can also be used for tracking the progression of a disease that influences the electrical stability of the myocardium. Additionally, a degree of the T-wave alternans (or more generally, magnitudes of alternation) can be used as an index of the level of risk for an impending ventricular arrhythmia.

Alternatively, the variation in T-wave amplitude of successive "high" T-waves and "low" T-waves can be measured in a sliding window. The amount of T-wave variation between the high and low T-waves can be used in conjunction with another measure of the beat-to-beat variation in T-waves of those beats where no change (induced or related to the pacing scheme) is expected. A third measure that determines the statistical significance of the difference in T-wave variations during pacing manipulations and in that during regular pacing or baseline can be used to determine the presence, degree, or absence of T-wave alternans.

In another example, the difference between the T-wave metrics (e.g., T-wave amplitudes) of successive beats following changes in beat length can be determined, and a histogram of the T-wave amplitude differences can be created. For example, assume T-wave amplitudes are measured for 4 beats that follow each change in beat length. For each 4 beat set, the difference between T-wave amplitudes of the 1st and 2nd beats, the 2nd and 3rd beats, and the 3rd and 4th beats can be determined. Then, it can be determined if the shape of the histogram forms a "double peak mountain" or an upside down "W" centered at about zero. This can be accomplished, e.g., by searching for local maxima's within the histogram. When two local maxima's are found at opposite polarities, e.g., at around +/−10.0 mV, there is a determination that T-wave alternans are present.

For this next example, assume that after each change in beat length, T-wave metrics of the next 4 beats are measured and stored in memory, until 50 changes in beat length are detected. This would result in T-wave metrics being obtained for a total of 200 T-waves. One option would be to ensemble average the 50 sets of 4 beats and come up with an averaged representation of a 4-beat set. The presence of T-wave alternans can then be determined from this 4-beat set.

Another option would be to determine, for each 4 beat set, the difference between T-wave amplitudes of the 1st and 2nd beats, the 2nd and 3rd beats, and the 3rd and 4th beats, resulting in three differences for each 4 beat set (i.e., a first difference between the metrics for 1st and 2nd beats, a second difference between the metrics for the 2nd and 3rd beats, and a third difference between the metrics for the 3rd and 4th beats). Assuming such differences (which are examples of magnitudes of alternation) are determined for each of 50 separate 4 beat sets, then the first difference of each of the 50 sets can be averaged to produce an average first difference, the second difference of each of the 50 sets can be averaged to produce an average second difference, and the third difference of each of the 50 sets can be average to produce an average third difference. The presence of T-wave alternans can then be determined from the average first difference, the average second difference and the average third difference.

These are just a few examples of the ways in which the presence of T-wave alternans can be detected at step 1006, based on the T-wave metrics measured at step 1004. One of ordinary skill in the art will appreciate that many other different techniques can be used, while still being within the spirit and scope of the present invention. For example, frequency domain techniques, which are known in the art, may also be used.

Specific embodiments described herein can be used by an implantable device to periodically monitor the relative changes/variations in repolarization pattern of the cardiac cycle as a surrogate measure of disease state and both short-term and long-term risk of arrhythmic events and SCD. When enabled, the algorithm paces the heart with a specific sequence designed to induce alternans at low heart rates. The pacing sequence, which may be any one of the above mentioned patterned pacing schemes, is designed to increase and decrease the amplitude (and duration) of T-waves at specific point(s) in the sequence. The detection algorithm takes advantage of this a priori knowledge about the impending increase or decrease in T-wave amplitude (and duration) in order to measure the amount of change in T-wave. By lining up all the beats where an increase in T-wave is expected, an ensemble average (or a modified version of averaging) of the "high" T-wave is calculated.

As explained above, the amount of beat to beat variation in T-waves can be used to determine the presence of alternans. In addition, it can be used as a measure of changes in electrical stability of the myocardium. The change in this measurement over time is used as a surrogate measurement of progression or regression of those diseases that have a direct influence on the electrical stability of the myocardium. When the algorithm determines that TWA is present, it can be indicative of heightened risk of ventricular arrhythmia. The device may be programmed to respond to the TWA result in a variety of ways.

More specifically, one or more response can be triggered if T-wave alternans are determined to be present. In accordance with an embodiment of the present invention, information related to the T-wave alternans can be stored. This can include, for example, storing amplitude, slope, timing, and/or duration information relating to the T-wave alternans. Such information can be continually, or from time to time, automatically uploaded to an external device (e.g., 102). Such an external device can be located, e.g., in the patients' home, and the information can be transmitted (e.g., through telephone lines or the Internet) to a medical facility where a physician can analyze the information. Alternatively, the external device can be located at a medical facility, and the information can be uploaded when the patient visits the facility.

As mentioned above, T-wave alternans are a known predictor of arrhythmic events such as tachyarrhythmias. Accordingly, in an embodiment, a patient is alerted (e.g., using alert 118) when T-wave alternans are detected. Such an alert could be a vibratory or auditory alert that originates from within the implantable device 10. Alternatively, the implantable device 10 may wirelessly transmit an alert to an external device that produces a visual or auditory alert that a patient can see or hear. The alert may inform that patient that he should rest, or if the patient is operating some type of dangerous machinery (e.g., a car), that the patient should stop what they are doing. By alerting the patient to rest, it is possible the a tachyarrhythmias may be avoided, or if it does occur, the patient will be less dangerous to themselves and others if the patient is resting when the tachyarrhythmias occurs (as opposed, e.g., to driving a car).

Additionally or alternatively, the patient can be instructed to take medication when alerted. In still another embodiment, a physician or other person (e.g., a caregiver, guardian or relative of the patient) is alerted whenever the presence of T-wave alternans is detected.

In further embodiments, therapy can be triggered in response to detecting the presence of T-wave alternans. One type of therapy would be for an implanted device (e.g., device 10) to stimulate the patient's vagus nerve, in an attempt to prevent an arrhythmia from occurring. In another embodiment, the implanted device, if appropriately equipped, can deliver appropriate drug therapy. In still another embodiment, the implanted device, if appropriately equipped, can deliver appropriate pacing therapy. In still another embodiment, the implantable device, if cable of delivering shock therapy, can begin to charge its capacitors in case the patient goes into ventricular fibrillation and needs shock therapy. These are just a few examples of the types of responses that can be performed upon detection of T-wave alternans. One of ordinary skill in the art would understand from the above description that other response are also possible, while still being within the spirit and scope of the present invention.

In further embodiments, changes in magnitudes of alternation are tracked thereby track changes in myocardial electrical stability. This can include recognizing increases in magnitudes of alternations as being indicative of increased electrical instability of the myocardium, and recognizing decreases in magnitudes of alternations as being indicative of increased electrical stability of the myocardium.

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

Example embodiments of the methods, systems, and components of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein.

Thus, the breadth and scope of the present invention should not be limited by any of the above-described exemplary embodiments, but should be defined only in accordance with the following claims and their equivalents.

What is claimed is:

1. In an implantable system, a method for monitoring myocardial electrical stability, comprising:
   (a) pacing a patient's heart in accordance with a pacing sequence that includes a short beat set including N short beats that get successively shorter from the beginning to the end of the short beat set, followed by a regular beat set including a plurality of regular beats, wherein N is an integer greater than 2, wherein each said short beat is shorter than each said regular beat, and wherein each said short beat and each said regular beat is shorter than the patient's intrinsic beat or the patient's normal pacing length;
   (b) measuring at least one metric of T-waves in two or more beats that follow each change in beat length;
   (c) determining magnitudes of alternation based on the measured T-wave metrics; and
   (d) monitoring myocardial electrical stability based on the determined magnitudes of alternation.

2. The method of claim 1, wherein step (d) comprises determining, based on the determined magnitudes of alternation, whether T-wave alternans are present.

3. The method of claim 1, wherein step (d) comprises tracking changes in the magnitudes of alternation as steps (a), (b) and (c) are repeated over time, to thereby track changes in myocardial electrical stability.

4. The method of claim 1, wherein each successive beat of the short beat set is a Δt shorter than the previous short beat.

5. The method of claim 1, wherein step (b) includes measuring at least one of the following T-wave metrics: T-wave amplitude; T-wave width; T-wave slope; T-wave area; T-wave morphology; QT interval; and evoked QT interval.

6. In an implantable system, a method for monitoring myocardial electrical stability, comprising:
   (a) pacing a patient's heart in accordance with a pacing sequence that includes a short beat set including N short beats that get successively shorter from the beginning to the end of the short beat set, followed by a long beat set including K long beats, followed by a regular beat set including M regular beats, wherein N, K, and M are integers greater than 2, wherein each said short beat is shorter than each said regular beat and each said regular beat is shorter than each said long beat, and wherein each said short beat, each said long beat, and each said regular beat is shorter than the patient's intrinsic beat or the patient's normal pacing length;
   (b) measuring at least one metric of T-waves in two or more beats that follow each change in beat length;
   (c) determining magnitudes of alternation based on the measured T-wave metrics; and
   (d) monitoring myocardial electrical stability based on the determined magnitudes of alternation.

7. The method of claim 6 wherein the plurality of long beats of the long beat set get successively shorter from the beginning to the end of the long beat set.

8. The method of claim 7 wherein each successive beat of the long beat set is a Δt shorter than the previous long beat.

9. The method of claim 6 wherein the plurality of long beats of the long beat set get successively longer from the beginning to the end of the long beat set.

10. The method of claim 9 wherein each successive beat of the long beat set is a Δt longer than the previous long beat.

11. The method of claim 6 wherein each successive beat of the short beat set is a Δt shorter than the previous short beat.

12. In an implantable system, a method for monitoring myocardial electrical stability, comprising:
   (a) pacing a patient's heart in accordance with a pacing sequence that includes a short beat set including N short beats that get successively longer from the beginning to the end of the short beat set, followed by a long beat set including K long beats, followed by a regular beat set including M regular beats, wherein N, K, and M are integers greater than 2, wherein each said short beat is shorter than each said regular beat and each said regular beat is shorter than each said long beat, and wherein each said short beat, each said long beat, and each said regular beat is shorter than the patient's intrinsic beat or the patient's normal pacing length;
   (b) measuring at least one metric of T-waves in two or more beats that follow each change in beat length;
   (c) determining magnitudes of alternation based on the measured T-wave metrics; and
   (d) monitoring myocardial electrical stability based on the determined magnitudes of alternation.

13. The method of claim 12 wherein the plurality of long beats of the long beat set get successively shorter from the beginning to the end of the long beat set.

14. The method of claim 13 wherein each successive beat of the long beat set is a Δt shorter than the previous long beat.

15. The method of claim 12 wherein the plurality of long beats of the long beat set get successively longer from the beginning to the end of the long beat set.

16. The method of claim 15 wherein each successive beat of the long beat set is a Δt longer than the previous long beat.

17. The method of claim 12 wherein each successive beat of the short beat set is a Δt longer than the previous short beat.

* * * * *